(12) United States Patent
Kim et al.

(10) Patent No.: US 8,530,639 B2
(45) Date of Patent: Sep. 10, 2013

(54) METHOD FOR ISOLATING A NUCLEIC ACID USING PARTICULATE MATTER AND A COMPOSITION THEREFOR

(75) Inventors: Jong-Hoon Kim, Seoul (KR); Min Kim, Daejeon (KR); Hae-Joon Park, Gyeonggi-do (KR); Han Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 846 days.

(21) Appl. No.: 12/448,134

(22) PCT Filed: Dec. 11, 2007

(86) PCT No.: PCT/KR2007/006393
§ 371 (c)(1),
(2), (4) Date: Mar. 9, 2010

(87) PCT Pub. No.: WO2008/072865
PCT Pub. Date: Jun. 19, 2008

(65) Prior Publication Data
US 2010/0197903 A1   Aug. 5, 2010

(30) Foreign Application Priority Data

Dec. 11, 2006  (KR) .................. 10-2006-0125864

(51) Int. Cl.
*C07H 21/00* (2006.01)
(52) U.S. Cl.
USPC ....................................................... 536/25.4
(58) Field of Classification Search
None
See application file for complete search history.

(56) References Cited

U.S. PATENT DOCUMENTS

| | | | |
|---|---|---|---|
| 5,075,430 A | 12/1991 | Little | |
| 5,155,018 A | 10/1992 | Gillespie et al. | |
| 5,658,548 A | 8/1997 | Padhye et al. | |
| 5,665,554 A | 9/1997 | Reeve et al. | |
| 5,777,098 A | 7/1998 | Gray et al. | |
| 5,804,684 A * | 9/1998 | Su | 536/25.4 |
| 5,808,041 A | 9/1998 | Padhye et al. | |
| 5,990,479 A | 11/1999 | Weiss et al. | |
| 6,136,083 A | 10/2000 | Schmidt et al. | |
| 6,255,477 B1 | 7/2001 | Kleiber et al. | |
| 6,274,386 B1 | 8/2001 | Harttig | |
| 6,545,143 B1 | 4/2003 | Harttig et al. | |
| 6,919,444 B2 | 7/2005 | Harttig et al. | |
| 2004/0229344 A1 | 11/2004 | Dunbar et al. | |
| 2005/0261486 A1* | 11/2005 | Grossman et al. | 536/23.1 |

FOREIGN PATENT DOCUMENTS

| | | |
|---|---|---|
| KR | 2003-0032915 | 4/2003 |
| KR | 2003-0038063 | 5/2003 |
| KR | 10-2006-0035684 | 4/2006 |

* cited by examiner

*Primary Examiner* — Lawrence E Crane
(74) *Attorney, Agent, or Firm* — Clark & Brody

(57) ABSTRACT

A method for isolating a nucleic acid from a biological sample includes applying particulate matter to promote co-aggregation and co-precipitation of insoluble aggregate by directly adding to the biological sample, adding to the biological sample in admixture with a cell lysis buffer, adding to the biological sample treated with a cell lysis buffer, adding to cell lysates in admixture with a buffer for forming denatured protein aggregate; or adding to cell lysates comprising the formed denatured protein aggregate. The particulate matter is selected from the group consisting of a material formed from an element of Ag, Fe, Ti, Al, Sn, Si, Cu, Mo, Ni, W or Zn, an oxide, a carbide, a nitride, a boride and a silicide thereof, and a mixture thereof, a polymer selected from PMMA (Poly Methyl MethAcrylate), polyethylene or polyurethane; and a mixture thereof. The insoluble aggregate comprises denatured protein aggregate and cell debris.

8 Claims, 4 Drawing Sheets

METHOD FOR ISOLATING A NUCLEIC ACID USING PARTICULATE MATTER AND A COMPOSITION THEREFOR

This is a national stage application based on PCT Application No. PCT/KR2007/006393, filed on Dec. 11, 2007, which claims priority from KR10-2006-0125864, filed on Dec. 11, 2006.

TECHNICAL FIELD

The present invention relates to a method for isolating a nucleic acid using particulate matter and a composition therefor, and more specifically, to a method for isolating a nucleic acid using particulate matter to rapidly and efficiently co-aggregate and co-precipitate insoluble denatured protein aggregate and cell debris formed during the isolation of a nucleic acid from a biological sample, thereby to remarkably shorten the time required for the isolation, and a composition for the isolation of a nucleic acid.

BACKGROUND ART

In 1979, Birnboim H. C, and Doly J. reported a method for extracting double-stranded plasmid DNA from *E. coli* by alkaline lysis method. In 1976, Blin N. and Stafford D. W. reported a method for isolating genomic DNA from eukaryotes. Further, in 1972, Aviv. H. and Leder P. reported a method for isolating messenger RNA by chromatography. Recently, as the requirement for a highly purified nucleic acid has been increased in various fields including biotechnology, diagnostics, pharmacology and metabolomics, attempts have been made to isolate a nucleic acid more rapidly and with a higher purity from a variety of biological samples.

The most advanced in the method for isolating a nucleic acid so far is a carrier to specifically adsorb a nucleic acid among various materials, e.g. genomic DNA, plasmid DNA, messenger RNA, protein and cell debris, in cell lysates. U.S. Pat. Nos. 5,075,430, 5,155,018, 5,658,548 and 5,808,041 disclose a method for isolating a nucleic acid with chaotropic salts, silica gel, micro silica particles, micro glass particles, micro glass fiber, micro silica fiber, micro silica fibrous membrane, hydrophilic membrane and anion exchange resin membrane. U.S. Pat. Nos. 5,665,554, 5,990,479, 6,136,083, 6,255,477, 6,274,386, 6,545,143, and 6,919,444 disclose a method for isolating a nucleic acid by modifying the surface of magnetic metallic particles, such as iron, zinc, etc., and adsorbing specifically an anionic nucleic acid thereto. As set forth above, almost all studies to develop a method for isolating a nucleic acid have been focused on the research and development of materials to adsorb a nucleic acid.

Commercial kits on the market adopt substantially the same methods as those described in the above references. Therefore, in order to rapidly isolate a nucleic acid with a high purity, there has been an eager demand on a new method to rapidly isolate only a desired nucleic acid from cell debris, denatured protein aggregate, and other various materials in cell lysates.

DISCLOSURE

Technical Problem

It is an object of the present invention to provide a method for isolating a nucleic acid using a composition comprising particulate matter to promote co-aggregation and co-precipitation of insoluble denatured protein aggregate and cell debris, thereby to precipitate insoluble aggregate and retain only a nucleic acid in a solution, upon centrifugation.

It is another object of the present invention to provide a composition for the isolation of a nucleic acid comprising particulate matter, to rapidly isolate a nucleic acid with a high purity from a biological sample.

Technical Solution

To achieve the above described objects, the present invention provides a method for isolating a nucleic acid, comprising the steps of lysing cells from a biological sample, and isolating a nucleic acid from insoluble aggregate comprising denatured protein aggregate and cell debris in cell lysates, characterized by using a particulate matter, the particulate matter promoting specifically co-aggregation and co-precipitation of insoluble aggregate. Preferably, the particulate matter has a mean particle diameter of 1 nm-1 mm, more preferably, of 10 nm-500 µm. To accelerate co-aggregation and co-precipitation of insoluble aggregate, the particulate matter preferably has a mean density of 1 g/cm$^3$-20 g/cm$^3$, and more preferably, of 2 g/cm$^3$-10 g/cm$^3$.

To achieve the above objects, the present invention provides a composition for the isolation of a nucleic acid, comprising particulate matter having a mean particle diameter of 1 nm-1 mm, preferably, of 10 nm-500 µm, which is selected from the group consisting of (a) an inorganic material selected from a material formed from an element of Ag, Fe, Ti, Al, Sn, Si, Cu, Mo, Ni, W or Zn, an oxide, a carbide, a nitride, a boride or a silicide thereof, or a mixture thereof; (b) a polymer selected from PMMA (Poly Methyl MethAcrylate), polyethylene or polyurethane; and, a mixture thereof.

The composition of the present invention is preferably an aqueous dispersion comprising one or more dispersing agents, in addition to the particulate matter, selected from the group consisting of alkoxylate, alkanolamide, ester, amine oxide, alkyl polyglycoside, polyacrylate, polymethacrylate, polyvinyl pyrrolidone, polyethyleneamine, polyvinylamine, betaine, glycinate, imidazoline and glycerol.

Hereinafter, the present invention will be described in detail.

Unless otherwise stated, the technical and scientific terms used herein can be understood by general meanings understood by one having an ordinary skill in the art.

The explanation on the same technical constitution and effect as the prior art is omitted herein.

The nucleic acid in the present invention refers to DNA (deoxyribonucleic acid) or RNA (ribonucleic acid), and includes genomic DNA, plasmid DNA, phage DNA, recombinant DNA, mRNA, rRNA, tRNA, recombinant RNA, microRNA and the like.

The method for isolating a nucleic acid according to the prior art herein refer to conventional centrifugation, vacuum manifold type, filtration, gravity separation or chromatography. Detailed explanations on these methods are omitted because these methods would be obvious to those skilled in the art.

The composition for the isolation of a nucleic acid of the invention refers to a reagent or buffer added in the step of lysing cells from a biological sample, or separating a nucleic acid and insoluble aggregate of denatured protein aggregate and cell debris from cell lysates. Specifically, the composition refers to a reagent or buffer, which is added in collecting and preserving a biological sample; added to a biological sample in admixture with a lysis buffer; added to a mixture of a biological sample and a lysis buffer; added to cell lysates in admixture with a buffer for forming denatured protein aggregate (i.e. neutralization buffer); or added to cell lysates comprising the formed denatured protein aggregate.

The present invention improves the efficiency of isolation of a nucleic acid by using particulate matter promoting co-aggregation and co-precipitation of denatured protein aggregate and cell debris.

The particulate matter for use in the present invention has a mean particle diameter of 1 nm-1 mm, more preferably, of 10 nm-500 μm. This is because it is technically difficult to produce particulate matter having a mean particle diameter of less than 1 nm, while particulate matter having a mean particle diameter of more than 1 mm would precipitate more rapidly than insoluble aggregate, and thus, could hardly give the desired effect. The particulate matter has a mean density of 1 $g/cm^3$-20 $g/cm^3$, preferably, of 2 $g/cm^3$-10 $g/cm^3$. Further, the particulate matter has a mean specific surface area of 1 $m^2/g$-20 $m^2/g$, and preferably, of 5 $m^2/g$ -15 $m^2/g$. If the particulate matter has a mean density of less than 1 $g/cm^3$, it could not effectively precipitate insoluble aggregate. On the contrary, if the particulate matter has a mean density of more than 20 $g/cm^3$, it would be heavier than insoluble aggregate, and thus, undesirably precipitate alone, not together with insoluble aggregate.

In the present invention, any of various materials can be used without limitation as the particulate matter, as long as it meets the criteria of mean particle diameter and/or density as described above. For example, an inorganic material selected from the group consisting of a material formed from an element of Ag, Fe, Ti, Al, Sn, Si, Cu, Mo, Ni, W or Zn, an oxide, a carbide, a nitride, a boride and a silicide thereof, and a mixture thereof; one or more polymer selected from the group consisting of PMMA (Poly Methyl MethAcrylate), polyethylene and polyurethane; and, a mixture thereof can be used.

Particularly, an inorganic material selected from the group consisting of a material formed from an element of Ag, Fe, Ti, Al, Sn, Si, Cu, Mo, Ni or W, an oxide, a carbide, a nitride, a boride and a silicide thereof, and a mixture thereof is more preferable because it gives a better effect for co-aggregating and co-precipitating insoluble aggregate formed during the isolation of a nucleic acid, and particulate matter formed from Fe, Ni, Si, $TiO_2$ or white quartz is the most preferable because it gives the much better effect than other materials.

The particulate matter of the present invention can be used as it is or as in an aqueous dispersion. Aqueous dispersion is more preferred since it reduces aggregation of particulate matter itself and is advantageous for experimental convenience. To prevent aggregation and precipitation of particulate matter itself, the aqueous dispersion can further comprise a dispersing agent for storage and use. The dispersing agent can be glycerol, alkoxylate, alkanolamide, ester, amine oxide, alkyl polyglycoside, polyacrylate, polymethacrylate, polyvinyl pyrrolidone, polyethyleneamine, polyvinylamine, betaine, glycinate and imidazoline, which may be used alone or in combination.

The content of particulate matter in an aqueous dispersion is not specially limited, but preferably 100 mg/ml-1,000 mg/ml, for experimental convenience. If the aqueous dispersion contains particulate matter of less than 100 mg/ml, it must have an increased volume, and so is inconvenient to handle. On the contrary, if the aqueous dispersion contains particulate matter of more than 1,000 mg/ml, it would have poorly dispersed particulate matter, and so is troublesome to handle.

A dispersing agent may be added to an aqueous dispersion containing particulate matter at an amount of 0.01-10.0% by volume, more preferably of 0.1-1.0% by volume. If the dispersing agent is added at an amount of less than 0.01% by volume, dispersing effect would not be satisfactory. Meanwhile, if the dispersing agent is added at an amount of more than 10.0% by volume, it may cause polymer-specific odor and decrease yield of the isolated nucleic acid.

In the method of isolating a nucleic acid, particulate matter of the present invention may be directly added to a biological sample, or added in admixture with a cell lysis buffer, to isolate a nucleic acid from insoluble aggregate. Otherwise, particulate matter may be added to cell lysates comprising the formed denatured protein aggregate, or added in admixture with a buffer for forming denatured protein aggregate. The direct addition of particulate matter to a biological sample or to a cell lysis buffer is more preferred in light of the isolation effect of a nucleic acid. In particular, the direct addition of particulate matter to a biological sample is the most preferred in light of the isolation effect of a nucleic acid.

The composition for isolation of a nucleic acid comprising particulate matter can be applied in the form of a nucleic acid extraction kit, in directly adding to a biological sample; adding to a biological sample together with a lysis buffer; adding to a mixture of a biological sample and a lysis buffer; adding to cell lysates together with a buffer for forming denatured protein aggregate; or adding to cell lysates comprising the formed denatured protein aggregate.

A biological sample of the present invention includes microorganisms such as bacteria, e.g. *E. coli*, yeast and cyanobacteria, animal tissues, plant tissues, blood, exudates, and transformants thereof transformed with a recombinant gene.

DESCRIPTION OF DRAWINGS

The above and other objects, features and advantages of the present invention will become apparent from the following description of preferred embodiments given in conjunction with the accompanying drawings, in which.

BEST MODE

Figure 1:
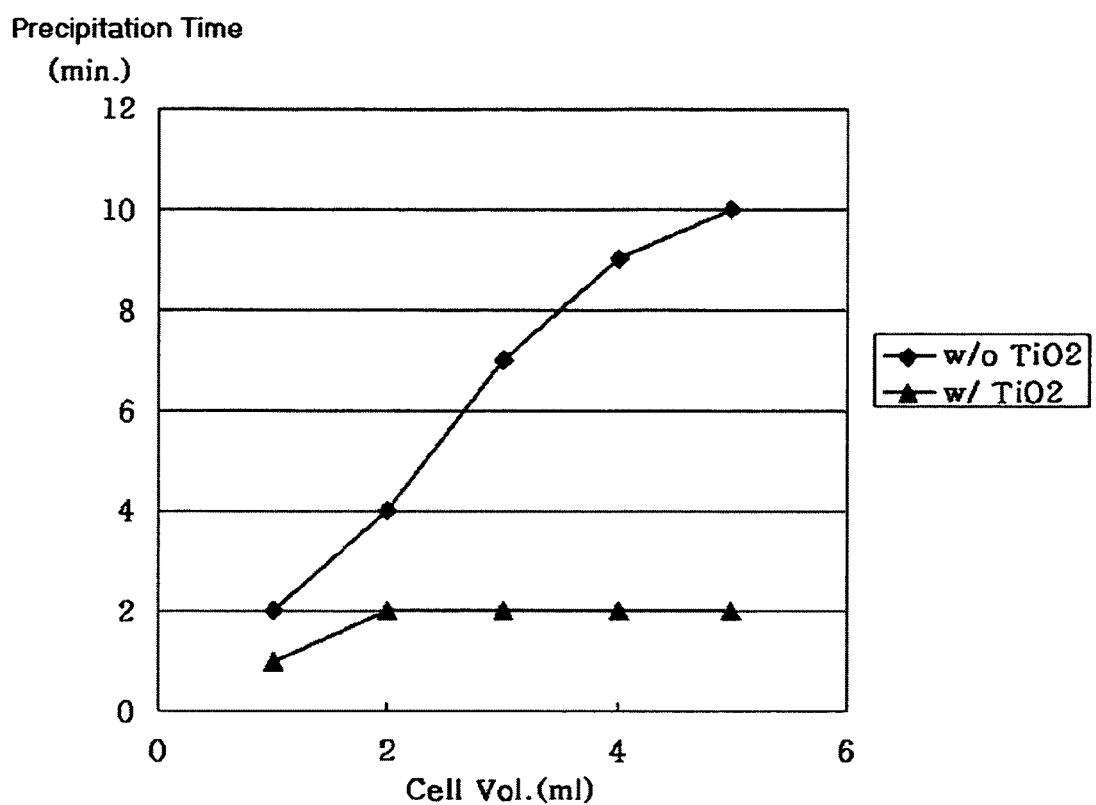
FIG. 1 is a graph comparing co-aggregation and co-precipitation of denatured protein aggregate and cell debris, with and without the addition of $TiO_2$ particles for the isolation of plasmid DNA from *E. coli* cells.

Hereinafter, the present invention will be specifically described with reference to the following examples, which are provided only for illustrative purpose, but should not be construed to limit the scope of the present invention in any manner. It will be appreciated that those skilled in the art, on consideration of this disclosure, may make modifications and improvements within the spirit and scope of the present invention.

EXAMPLE 1

Evaluation of an Effect of the Addition of Particulate Matter on Co-aggregation and Co-precipitation of Denatured Protein Aggregate and Cell Debris <1-1> Preparation of a Composition Comprising Particulate Matter As particulate matters of the present invention, $TiO_2$ particles were purchased from Nano Chemical Inc., Korea, Fe particles were purchased from Nano Technology Inc., Korea, Ni particles were purchased from NT Base Co., Ltd., Korea, and Si and white quartz particles were purchased from Sigma-Aldrich, respectively. The mean particle diameter and density of each particulate matter are shown in Table 1.

TABLE 1

|  | Fe | TiO$_2$ | Ni | Si | White quartz |
|---|---|---|---|---|---|
| Mean particle diameter | 100 nm | 250 nm | 100 nm | 50 μm | 300 μm |
| Mean particle density (g/cm$^3$) | 7.9 | 4.5 | 8.9 | 2.33 | 2.65 |
| Color | Black | White | Black | Black | White |

Each particulate matter was introduced into sterilized ultra pure water at a concentration of 500 mg/ml. Polyacrylate dispersing agent (KOSANT A-40, Chung Woo Fine Chemical Co., Ltd., Korea) was added to the aqueous dispersion containing 500 mg/ml of the particulate matter to 0.1% by volume, to give a composition comprising each particulate matter.

<1-2> Measurement of Co-aggregation and Co-precipitation of Denatured Protein Aggregate and Cell Debris with the Addition of the Particulate Matter In order to investigate co-aggregation and co-precipitation of denatured protein aggregate and cell debris, a kit for extracting plasmid DNA from *E. coli* (Cat. No. K-3030) was purchased from Bioneer Co., Korea, and it was used according to the manufacturer's instructions.

As an experimental material, *E. coli* XL-1 Blue strain transformed with pBluescript SK(+) vector (Stratagene) of 3.0 kb containing ampicillin resistant gene was used. The cells were inoculated in an LB liquid medium containing 100 μg/ml of ampicillin, and then, cultured with shaking at 37° C. for 16 hours until OD$_{600}$ value reached 2.0. 1 mL, 2 mL, 3 mL, 4 mL and 5 mL of the *E. coli* culture broth were centrifuged to isolate *E. coli* cells therefrom. Then, the supernatant was discarded therefrom to obtain the *E. coli* cells.

An experiment was performed according to the following protocol. A buffer containing RNase A was added to the obtained *E. coli* cells. After dispersing the cells well, a cell lysis buffer was added thereto, and then, mixed well. Finally, a neutralization buffer was added thereto and mixed well. The mixture was centrifuged at 13,000 rpm at room temperature. Further, to investigate the precipitation pattern with the addition of particulate matter, the composition containing TiO$_2$ particles prepared in Example <1-1> was added to the *E. coli* cells at an amount of 10 mg per reaction. The cells were well mixed with the composition of particulate matter with a vortex mixer. According to the above-described method, a cell lysis buffer and a neutralization buffer were added thereto sequentially, and the mixture was centrifuged at 13,000 rpm at room temperature. The time required for centrifugation to completely co-aggregate and co-precipitate denatured protein aggregate and cell debris was calculated to evaluate an effect of the addition of particulate matter on co-aggregation and co-precipitation. The results are shown in FIG. 1.

As shown in FIG. 1, without the addition of TiO$_2$ particles, the time required for co-aggregation and co-precipitation of denatured protein aggregate and cell debris increased from 2 minutes to 10 minutes, as the amount of *E. coli* cells increased from 1 ml to 5 ml. On the contrary, with the addition of TiO$_2$ particles, only 1-2 minutes were required for co-aggregation and co-precipitation, even as the amount of the cells increased from 1 ml to 5 ml.

EXAMPLE 2

Evaluation of an Effect of Particulate Matter on Co-aggregation and Co-precipitation of Insoluble Aggregate, Depending on the Step of Adding Particulate Matter The particulate matter was used at any of the following 5 different steps. First, it was added directly to a biological sample not yet treated with a cell lysis buffer. Second, it was added to a biological sample in admixture with a cell lysis buffer. Third, it was added to a biological sample treated with a cell lysis buffer. Fourth, it was added to cell lysates in admixture with a buffer for forming denatured protein aggregate. Fifth, it was added to cell lysates comprising the formed denatured protein aggregate.

To reveal the most effective condition for precipitating denatured protein aggregate and cell debris, 10 mg of the composition comprising 500 mg/ml of TiO$_2$ particles prepared in Example <1-1> was added to 5 ml of *E. coli* cells in each of the above steps. The time required for centrifugation was calculated in the same manner as described in Example <1-2>, to investigate the precipitation pattern of denatured protein aggregate and cell debris, depending on the step of adding particulate matter. The results are shown in FIG. 2.

Figure 2:
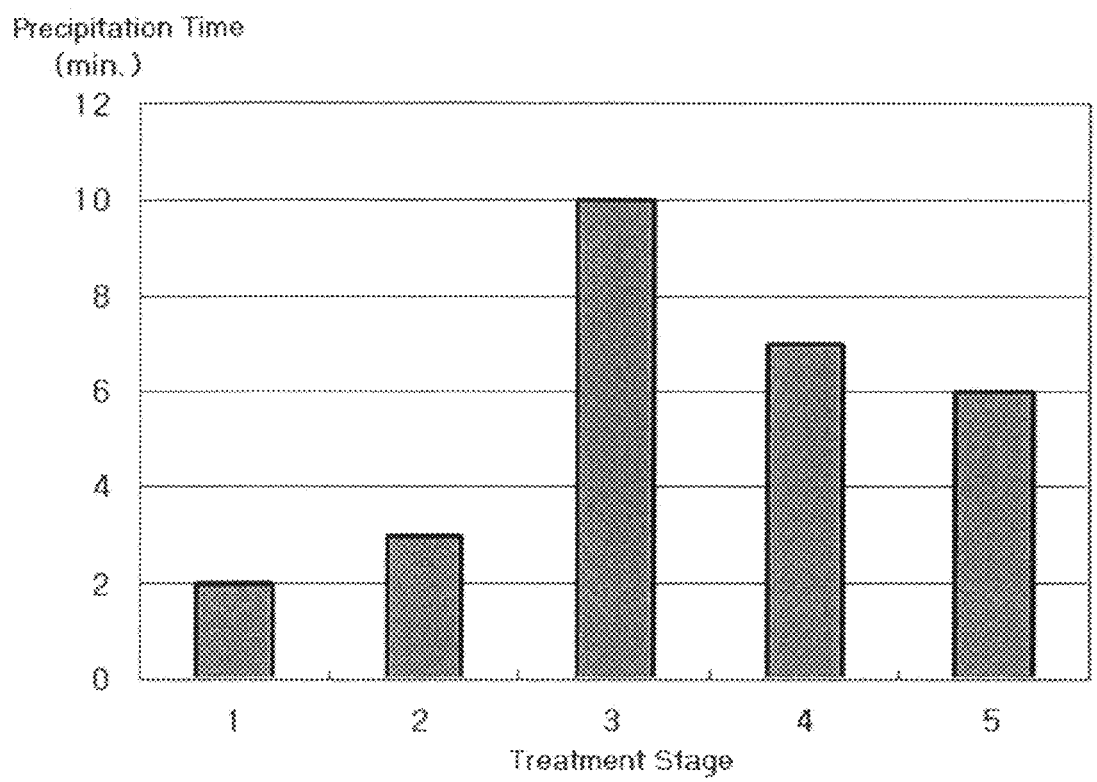
FIG. 2 is a graph comparing co-aggregation and co-precipitation of denatured protein aggregate and cell debris, depending on the step of adding $TiO_2$ particles for the isolation of plasmid DNA from *E. coli* cells.

As shown in FIG. 2, when the particulate matter was directly added to the biological sample (1), the shortest time, i.e. only 2 minutes, was required, and when the particulate matter was added in admixture with the cell lysis buffer (2), the second shortest time was required, for co-aggregation and co-precipitation of denatured protein aggregate and cell debris. Meanwhile, the effect to shorten the time was negligible when the particulate matter was added to the biological sample treated with the cell lysis buffer (3). In addition, when the particulate matter was added in admixture with the neutralization buffer (4) and after the addition of the neutralization buffer (5), TiO$_2$ particles slightly promoted co-aggregation and co-precipitation of denatured protein aggregate and cell debris.

Therefore, it was concluded that TiO$_2$ particles could shorten the time required for co-aggregation and co-precipitation of denatured protein aggregate and cell debris in the following order: direct addition to a biological sample not yet treated with a cell lysis buffer>addition to a biological sample together with a cell lysis buffer>addition to cell lysates after the addition of a neutralization buffer>addition to cell lysates together with a neutralization buffer>addition to a biological sample treated with a cell lysis buffer.

EXAMPLE 3

Comparison of the Total Time and Yield for the Isolation of a Nucleic Acid with and without the Addition of Particulate Matter 5 mL of *E. coli* cells were prepared according to the method of Example <1-2>. 10 mg of the aqueous dispersion of particulate matter prepared in the manner as described in Example <1-1> was added thereto per reaction. The total time required for isolating plasmid DNA was measured to evaluate an effect of the addition of particulate matter on the time required for the isolation. Absorbance of the solution comprising the isolated plasmid DNA was measured with a UV-spectrophotometer, to calculate typical yield. The results are shown in FIG. 3.

Figure 3:
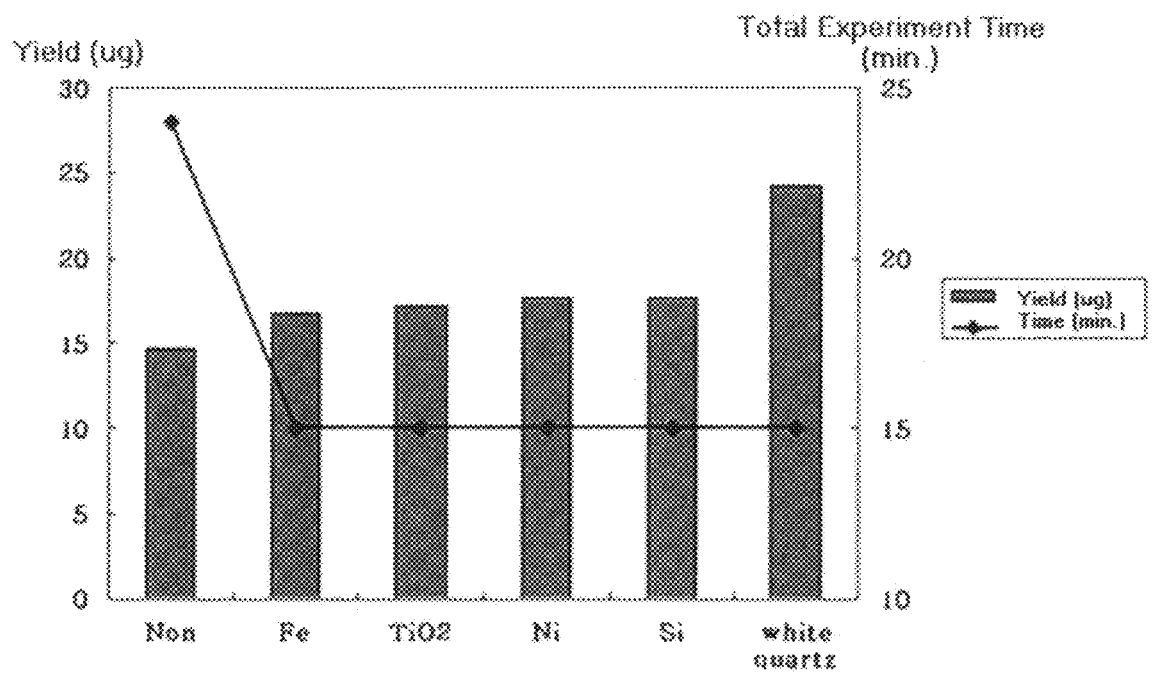
FIG. 3 is a graph comparing the time and yield for the isolation of plasmid DNA from *E. coli* cells, according to the present invention and the prior art.

As shown in FIG. 3, in the control non-treated with particulate matter (Non), yield of the isolated plasmid DNA was 15 μg, and the total time required for isolating plasmid DNA was 28 minutes. Meanwhile, in the groups treated with particulate matter including $TiO_2$ particles, the yield was 17 μg-24 μg and the time required was about 15 minutes, showing that the addition of particulate matter could shorten the time and increase the yield for isolating a nucleic acid from a biological sample.

EXAMPLE 4

Investigation on Whether or not Particulate Matter Inhibits Enzymatic Activities on an Isolated Nucleic Acid from a Biological Sample 1 μg of the isolated plasmid DNA in Example 3 was digested with 1 unit of Hind III (Cat. No. E-1721) purchased from Bioneer Co., Korea at 37° C. for 1 hour. The digested plasmid DNA was separated on a 1.0% agarose gel to confirm whether the digested plasmid DNA had the expected size of 3.0 kb, thereby to investigate whether or not the composition for the isolation of a nucleic acid comprising particulate matter of the present invention inhibits enzymatic activities. The results are shown in FIG. 4.

Figure 4:
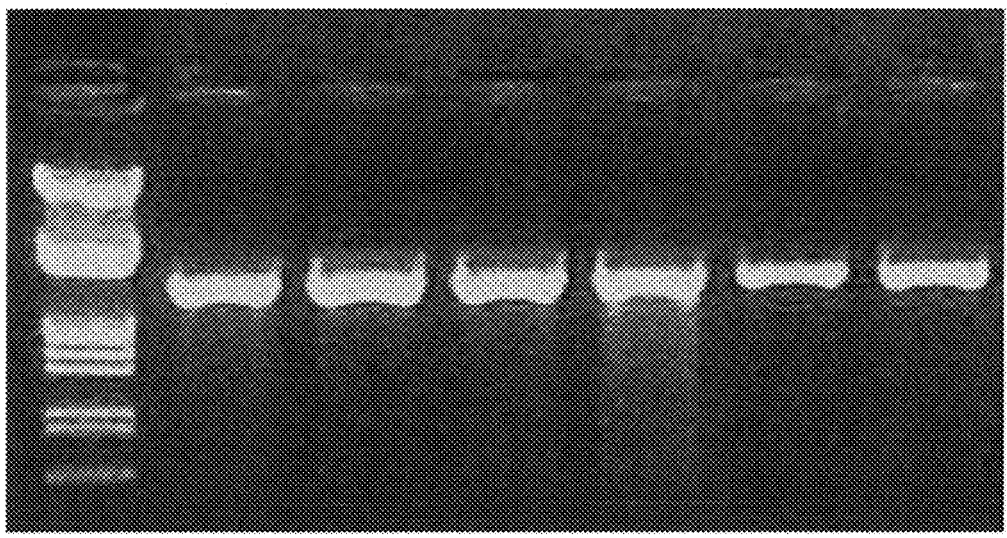
FIG. 4 is a photograph showing the result of electrophoresis on an agarose gel for plasmid DNA isolated from *E. coli* cells according to the present invention, and then, treated with a restriction enzyme.

In FIG. 4, M is the size marker; lane 1 is the control non-treated with particulate matter; lane 2 is the experimental group treated with Fe particles; lane 3 is the experimental group treated with $TiO_2$ particles; lane 4 is the experimental group treated with Ni particles; lane 5 is the experimental group treated with Si particles; and lane 6 is the experimental group treated with white quartz particles.

As shown in the electrophoretic photograph of FIG. 4, the experimental groups treated with particulate matter had the same size of plasmid DNA as the control non-treated with particulate matter, showing that particulate matter did not inhibit enzymatic activities on the isolated plasmid DNA at all.

[Industrial Applicability]

Particulate matter of the present invention can promote co-aggregation and co-precipitation of insoluble aggregate comprising denatured protein aggregate and cell debris formed during the isolation of a nucleic acid from a biological sample, thereby to remarkably shorten the time for centrifugation and so the total working time for isolation. Therefore, the present invention provides a method for isolating a nucleic acid using particulate matter specifically promoting co-aggregation and co-precipitation of insoluble denatured protein aggregate and cell debris, to remarkably shorten the time for isolation a nucleic acid from a biological sample, as well as to increase the efficiency of isolation of a nucleic acid from a large amount of a biological sample.

The invention claimed is:

1. A method for isolating a nucleic acid from a biological sample, comprising the steps of:
   lysing cells from a biological sample; and
   isolating a nucleic acid from insoluble aggregate comprising denatured protein aggregate and cell debris in cell lysates, characterized by applying particulate matter formed from Fe, Ni, Si, $TiO_2$ or white quartz to promote co-aggregation and co-precipitation of the insoluble aggregated by carrying out one of the following steps:
   (a) directly adding the particulate matter to the biological sample;
   (b) adding the particulate matter to, and mixing with, the biological sample and a cell lysis buffer;
   (c) adding the particulate matter to the biological sample previously treated with a cell lysis buffer;
   (d) adding the particular matter to cell lysates in admixture with a buffer which forms denatured protein aggregate; or
   (e) adding the particulate matter to cell lysates comprising a preformed denatured protein aggregate,
   wherein the particulate matter is dispersed in an aqueous solution comprising a dispersing agent selected from the group consisting of an alkoxylate, an alkanolamide, an ester, an amine oxide, an alkyl polyglycoside, polyacrylate, a polymethcacrylate, a polyvinyl pyrrolidone, a polyethyleneamine, polyvinylamine, a betaine, a glycinate, imidazoline and glycerol,
   wherein the nucleic acid is isolated from the insoluble aggregate by centrifugation, vacuum manifold type filtration, gravity separation or chromatography.

2. The method for isolating a nucleic acid according to claim 1, wherein the particulate matter has a mean particle diameter of 1 nm -1 mm.

3. The method for isolating a nucleic acid according to cliam 2, wherein the particulate matter has a mean particle diameter of 10 nm 500 μm.

4. The method for isolating a nucleic acid according to claim 3, wherein the particulate matter has a mean density of 1 $g/cm^3$ - 20 $g/cm^3$.

5. The method for isolating a nucleic acid according to claim 4, wherein the particulate matter has a mean density of 2 $g/cm^3$ - 10 $g/cm^3$.

6. A composition for the isolation of a nucleic acid, comprising particulate matter having a mean particle diameter of 1 mm - 1 mm, formed from Fe, Ni, Si, $TiO_2$ or white quartz, and dispersed in an aqueous solution comprising a dispersing agent selected from the group consisting of an alkoxylate, an alkanolamide, an ester, and amine oxide, an alky polyglycoside, a polycrylate, a polymethacrylate, a polyvinyl pyrrolide, a polyethyleneamine, a polyvinylamine, a betaine, a glycinate, imidazoline and glycerol.

7. The composition for the isolation of a nucleic acid accordinq to claim 6, wherein the particulate matter has a mean particle diameter of 10 mn - 500 μm and a mean density of 2 $g/cm^3$ - 10 $g/cm^3$.

8. An aqueous dispersion containing 0.1 - 1.0% by volume of one or more dispersing agents selected from the group consisting of an alkoxylate, an alkanolamide, an ester, an amine oxide, an alkyl polyglycoside, a polyacrylate, a polymetnacrylate, a polyvinyl pyrrolidone, a polyethyleneamine, a polyvinylamine, a betaine, a glycinate, imidazoline and glycerol for the isolation of a nucleic acid, comprising particulate matter having a mean particle diameter of 1 nm - 1 mm, formed from Fe, Ni, Si, $TiO_2$ or white quartz.

\* \* \* \* \*